(12) United States Patent
Hardie et al.

(10) Patent No.: US 9,733,322 B2
(45) Date of Patent: Aug. 15, 2017

(54) SIGNAL TRANSMISSIONS TO AND FROM A LOCAL COIL OF A MAGNETIC RESONANCE SYSTEM

(71) Applicants: Donald Hardie, Möhrendorf (DE); Stefan Popescu, Erlangen (DE)

(72) Inventors: Donald Hardie, Möhrendorf (DE); Stefan Popescu, Erlangen (DE)

(73) Assignee: Siemens Aktiengesellschaft, München (DE)

( * ) Notice: Subject to any disclaimer, the term of this patent is extended or adjusted under 35 U.S.C. 154(b) by 539 days.

(21) Appl. No.: 14/287,662

(22) Filed: May 27, 2014

(65) Prior Publication Data

US 2014/0361769 A1 Dec. 11, 2014

(30) Foreign Application Priority Data

Jun. 5, 2013 (DE) .................. 10 2013 210 381

(51) Int. Cl.
*G01V 3/00* (2006.01)
*G01R 33/34* (2006.01)
(Continued)

(52) U.S. Cl.
CPC ......... *G01R 33/34* (2013.01); *G01R 33/3692* (2013.01); *A61B 5/055* (2013.01); *G01R 33/3415* (2013.01)

(58) Field of Classification Search
CPC ......... G03G 2215/1695; G03G 15/161; G03G 15/1605; G03G 15/24; G03G 2215/0119
(Continued)

(56) References Cited

U.S. PATENT DOCUMENTS 3,732,508 A 5/1973 Ito et al.
4,386,365 A * 5/1983 Gargini .................. H04H 20/77
348/14.11
(Continued)

FOREIGN PATENT DOCUMENTS

DE 202011105135 U1 12/2011

OTHER PUBLICATIONS

German Office Action cited in DE102013210381.6, mailed Oct. 17, 2013.
(Continued)

*Primary Examiner* — Walter L Lindsay, Jr.
*Assistant Examiner* — Frederick Wenderoth
(74) *Attorney, Agent, or Firm* — Lempia Summerfield Katz LLC (57) ABSTRACT

Described is a local coil having a number of magnetic resonance antenna elements, a, strip-shaped, metamaterial signal conductor, and an adapter device for coupling signals into the metamaterial signal conductor and/or coupling signals out of the metamaterial signal conductor. Additionally described is a magnetic resonance system having a local coil communication interface and an adapter device for coupling signals out of a metamaterial signal conductor and transferring them to the local coil communication interface and/or for coupling signals from the local coil communication interface into a metamaterial signal conductor, and a method for transmitting signals between a local coil and a local coil communication interface of a magnetic resonance system.

15 Claims, 5 Drawing Sheets (51) Int. Cl.
*G01R 33/36* (2006.01)
*A61B 5/055* (2006.01)
*G01R 33/3415* (2006.01)

(58) Field of Classification Search
USPC .......................................................... 324/307
See application file for complete search history.

(56) References Cited

U.S. PATENT DOCUMENTS

| | | | |
|---|---|---|---|
| 2002/0123701 A1* | 9/2002 | Eriksen | A61B 5/06 600/595 |
| 2009/0270951 A1* | 10/2009 | Kallmyer | A61N 1/3787 607/61 |
| 2010/0039111 A1* | 2/2010 | Luekeke | G01R 33/341 324/318 |
| 2011/0117202 A1* | 5/2011 | Bourke, Jr. | H05B 41/2806 424/490 |
| 2012/0161768 A1 | 6/2012 | Hardy et al. | |

OTHER PUBLICATIONS

Hendry, Isolation of the Zenneck Surface Wave, Nov. 2010, pp. 613-616, Antennas and Propagation Conference (LAPC).

Turner et al., A Novel Technique Enabling the Realisation of 60 GHz Body Area Networks, Proceedings of the 2012 Ninth International Conference on Wearable and Implantable Body Sensor Networks, 2012, pp. 58-62, IEEE Computer Society, Washington D.C.

\* cited by examiner

SIGNAL TRANSMISSIONS TO AND FROM A LOCAL COIL OF A MAGNETIC RESONANCE SYSTEM

CROSS-REFERENCE TO RELATED APPLICATIONS

This application claims the benefit of DE 10 2013 210 381.6, filed on Jun. 5, 2013, which is hereby incorporated by reference in its entirety.

TECHNICAL FIELD

The embodiments relate to local coils for a magnetic resonance system having a number of magnetic resonance antenna elements. The embodiments also relate to a magnetic resonance system having a local coil communication interface. The embodiments furthermore relate to methods for transmitting signals between a local coil and such a local coil communication interface of a magnetic resonance system.

BACKGROUND

In order to obtain image data (magnetic resonance recordings) during magnetic resonance imaging from an area from the inside of the body of an examination object, the body or the body part to be examined is exposed to a static main magnetic field (e.g., referred to as $B_0$ field) that is as homogeneous as possible. As a result, the macroscopic magnetization within the body is aligned parallel to the direction of the $B_0$ field, e.g., the z direction. In addition, radio-frequency antennas are used to radiate radio-frequency pulses into the examination object, the frequency of which being in the range of the resonant frequency, what is known as Larmor frequency, of the nuclei to be excited (e.g., hydrogen nuclei) in the present magnetic field. Therefore, the radio-frequency pulses will be referred to below as magnetic resonance radio-frequency pulses. The magnetic flux density of the radio-frequency pulses may be designated as $B_1$ (and the transmitted RF signals therefore also as $B_1$ field, in short). With the aid of the radio-frequency pulses, the macroscopic magnetization within the examination object is excited such that it is deflected out of its equilibrium position parallel to the main magnetic field $B_0$ by what is known as a "flip angle." The macroscopic magnetization then proceeds about the z-direction and relaxes gradually. The in-phase movement of the microscopic spin about the precession cone may be considered to be macroscopic nucleus magnetization in the x/y plane (perpendicular to the z-direction). The magnetic resonance measurement signals generated during the relaxation of the nucleus magnetization are recorded as what is called "raw data" using radio-frequency receiver antennas. The magnetic resonance images of the examination object are finally reconstructed on the basis of the acquired raw data, where spatial encoding is carried out with the aid of rapidly switched gradient magnetic fields that are superposed on the main magnetic field during the transmission of the magnetic resonance radio-frequency pulses and/or the acquisition of the raw data.

The magnetic resonance raw data are recorded in most cases with the aid of the local coils, which are positioned directly on, at, or under the examination object, e.g., the patient or subject. This has, among others, the advantage that the signal-to-noise ratio may be significantly increased and that a better image quality may be achieved. In some cases, local coils are also used for transmitting the $B_1$ field. Especially when recordings of a relatively large spatial region are intended to be made, a large number of such local coils are used. In many examinations, for example, the patient is completely covered by individual local coils, for example, head coils, chest coils, stomach coils, leg coils, etc.

For transmitting signals between the local coils and the local coil communication interface arranged fixedly in the magnetic resonance system, cables may be used. In the following text, a local coil communication interface is understood to describe any desired arrangement of magnetic resonance transmitting and/or receiving devices, e.g., corresponding interfaces for transmitting the $B_1$ field and for receiving the raw data, and of control devices for the local coils for transmitting control signals to the local coils, for example, for switching from transmitting operation to receiving operation, for detuning, etc., and/or for receiving status signals therefrom. In the process, all these components may be integrated in a common device, or they may be spatially separate devices.

The cables have a relatively thick electrical insulation to protect the patient against excessive heating, such as for transmitting the radio-frequency signals. In addition, the radio-frequency cables have, at relatively short spacings (for example, every 30 cm in the case of a 3 Tesla lamp magnetic resonance system), relatively voluminous sheath wave barriers in order to prevent radio-frequency currents from passing over the cable shielding. This may in turn lead to interference with the $B_1$ field. Another problem lies in the fact that the local coils may have to be coupled via relatively expensive multiway radio-frequency connectors to the corresponding devices of the local coil communication system of the magnetic resonance system. The radio-frequency connectors are additionally constructed such that they are protected against contamination from various liquids, as may occur during clinical operation, by way of suitable mechanical seals, etc., in particular if no cable is inserted. Another disadvantage of the cabling is that the preparation of a patient for examination is time-consuming on account of the relatively high effort in positioning the local coils, the subsequent fixing, and subsequently the necessary cabling.

In order to reduce the outlay, it has already been suggested to transmit various signals (and, in some embodiments, the measured raw data), wirelessly from the local coils. However, since the number of local coils used or of their channels continuously increases with the improvement of the examination capabilities (currently, receiving coils with 32 channels or even 64 channels are already used as a matter of routine, for example), the required bandwidth for the signal transmission also increases correspondingly, and may even exceed the currently still freely available signal bandwidth. Such radio transmission systems additionally have the disadvantage that a redundant transmission via a plurality of channels may be necessary, since multiple reflections at the metallic structures within the measurement space of the scanner may take place.

In U.S. Publication No. 2012/0161768 A1, a solution was additionally suggested, in which the flexible microstrip conductors are incorporated within a blanket or item of clothing, which are connected to the local coils with the signals being transmitted via the microstrip conductors (stripline). However, the microstrip conductors are constructed as electrical conductors, such that transmission both of radio-frequency signals and of DC current is possible. Even with such conductors, provisions similar to sheath wave barriers are therefore taken such that no interference fields may occur, in particular in the kHz range, the frequency range of the gradient coils.

SUMMARY AND DESCRIPTION

The scope of the present invention is defined solely by the appended claims and is not affected to any degree by the statements within this summary. The present embodiments may obviate one or more of the drawbacks or limitations in the related art.

It is therefore an object of the embodiments to specify a suitable local coil and a suitable magnetic resonance system and an alternative method for transmitting signals from and to the local coils, with which the abovementioned problems are at least reduced or, in some instances, avoided entirely.

A local coil may have a number of magnetic resonance antenna elements, e.g., at least one magnetic resonance antenna element, and, in some embodiments, more than one magnetic resonance antenna element. The magnetic resonance antenna elements may be transmitting and receiving antenna elements. However, the magnetic resonance antenna elements may be at least receiving antenna elements. The local coil is equipped with a metamaterial signal conductor. Additionally, the local coil has an adapter device, for example, a coupling-in and/or coupling-out device, for coupling signals into the metamaterial signal conductor and/or for coupling signals out of the metamaterial signal conductor.

What are known as "metamaterials" are relatively recent artificially manufactured structures, the permeability of which for electrical and magnetic fields differs from what may take place naturally. One specific characteristic of metamaterials is their frequency-selective behavior. A metamaterial may be constructed such that the metamaterial transmits electromagnetic waves within a specific frequency band of the electromagnetic spectrum. As will be explained further below, various metamaterials are already available, which permit the transmission within the radio-frequency bands, with some including frequencies of magnetic resonance signals in the megahertz range. To date, proposals have been made to use metamaterials acting in the magnetic resonance frequency range in magnetic resonance antennas themselves, for example in U.S. Publication No. 2010/0039111 A1 for planar antenna structures, or in DE 20 2011 105 135 U1 for constructing traveling wave antenna structures. Additionally, metamaterials that operate in the microwave or terahertz band range or even in the infrared or visible light range are already available. In the context herein, a metamaterial is taken to describe a material having a structure that was produced artificially in such a way and permit a correspondingly delimited frequency-selective transmission of electromagnetic waves. This is achieved by specially produced, or periodic, fine structures (cells, individual elements) of (di)electric or magnetically active materials inside the structures. The size of the cells is dependent on the wavelength. At high frequencies, polyvinyl chloride (PVC), which has an artificial molecular structure, may optionally be used as a metamaterial. Metamaterials for the frequency range of the magnetic resonance signals (10-500 MHz) may be realized from discrete components (capacitors, coils etc.) and thus achieve a cell size in the centimeter range. The metamaterials are thus relatively rigid and thick. The metamaterials may operate in a frequency range above approximately 10 GHz (e.g., in the microwave, terahertz or infrared range) and may be relatively thin (e.g., between 1 and 500 µm, where the exact thickness is dependent on the frequency range) and therefore flexible. The metamaterials may be connected to or integrated easily in various flexible materials, for example belts, blankets or items of clothing and the like. The metamaterial conductor may be constructed in a strip-shaped manner such that the signals are transmitted only along the strip.

The adapter device serves for connecting a metamaterial strip to, for example, a flat signal-processing module (PCB). The adapter permits nearly lossless signal coupling-in or coupling-out and may be realized similarly, as is described in U.S. Pat. No. 3,732,508, for a coaxial-to-stripline adapter, to which reference is made in this context. Another possible adapter is, for example, the Waveguide to SMA model V4607, Narda Microwave—East, 435 Moreland Road Hauppauge, N.Y. 11788, USA.

A magnetic resonance system accordingly has a local coil communication interface, e.g., corresponding magnetic resonance or radio-frequency transmitting and/or receiving devices and a control device for local coils, etc. The magnetic resonance system additionally has a suitable adapter device for coupling signals out of a metamaterial signal conductor and for transferring the signals to the local coil communication interface and/or for coupling signals from the local coil communication interface into a metamaterial signal conductor. Owing to this adapter device, which includes a corresponding coupling-in and/or coupling-out device, for example in connection with the adapter on the local coil, the magnetic resonance system or its components that are associated with the local coil communication interface may communicate with a local coil via a metamaterial signal conductor.

The magnetic resonance system may thus be correspondingly equipped with a local coil arrangement having a number of local coils. It is possible for there to be one or more local coils. In principle the local coil arrangement may additionally also have a number of the local coils and additional local coils, which communicate via conventional cables or wirelessly with the local coil communication interface of the magnetic resonance system.

In a method for transmitting signals, in particular control signals, radio-frequency transmitting signals ($B_1$ pulses) and/or magnetic resonance signals, (e.g., raw data), between a local coil and a local coil communication interface of the magnetic resonance system, the signals may be transmitted via a strip-shaped metamaterial signal conductor. The use of a metamaterial signal conductor for transmitting the desired signals between a local coil and the local coil communication interface has the advantage that no voluminous and expensive radio-frequency cables, sheath wave barriers and connectors need to be used. The method consequently leads to lower costs and significantly more lightweight local coils. With a suitable construction of the metamaterial, signals may be transmitted in a high bandwidth, where only a substantially two-dimensional transmission, (e.g., along the metamaterial strips), is possible. In contrast to radio transmission of electromagnetic waves that takes place freely in space, no interference or blocking need be feared. Multiple transmission path problems owing to reflections on metallic structures, such as for example the internal tube of the magnetic system (or of what is known as the "outer vacuum container" OVC), may not occur.

As will be described below, a very flexible communication network may be established using the metamaterial signal conductors, where the entire system may be set up and maintained easily and in particular, the local coils may be positioned easily. Depending on the exact architecture and the selected network protocol of the communication network, it is also possible to realize bidirectional communication between the local coils and the local coil communication interface of the magnetic resonance system.

The metamaterial signal conductor may be constructed such that the conductor has a high-pass or bandpass characteristic with a stopband below 10 GHz, below 15 GHz, or below 20 GHz. The stopband is here considered to be that range that is below the respectively indicated cut-off frequency, e.g., in which the signal is strongly attenuated (e.g., an attenuation of at least 3 dB, or at least 10 dB). Within the bandpass ranges or above the cut-off frequency, the conductor may be permeable, e.g., the conductor has low attenuation (such as less than 3 dB).

The metamaterial may be constructed such that transmission of signals are above 14 GHz and below 100 GHz, or in the range of the 60 GHz band, e.g., in the suggested standard IEEE 802.11ad for wireless communication. Transmission within the GHz range has the advantage that the signal transmission along the metamaterial signal conductors do not overlap with the primary magnetic resonance signals that may be in the MHz range. In that case, the metamaterial acts like an insulator for the magnetic resonance signals, as a result of which local heating effects of the metamaterial signal conductors may be completely avoided. Since no local heating may occur, such metamaterial signal conductors may also be guided in relative proximity along the skin of the patient. In addition, the losses in radio-frequency currents are reduced, which may otherwise lead to interference with the transmitted $B_1$ field.

The metamaterial signal conductor may be constructed such that the signal conductor forms a surface wave conductor. The metamaterial signal conductor may be arranged correspondingly on the surface such that it is possible to couple signals into and/or out of the metamaterial signal conductor at each location on the surface along the metamaterial signal conductor, e.g., along the entire strip-shaped surface of the metamaterial signal conductor. The surface waves may be, for example, what are known as "Zenneck waves", as are described in Janice Hendry, "Isolation of the Zenneck Surface Wave," published in: Antennas and Propagation Conference (LAPC), 2010 Loughborough, Date of Conference: Nov. 8-9, 2010, page(s): 613-616, Print ISBN: 978-1-4244-7304-5, INSPEC Accession Number: 11696206). Explicit reference to this article is also made with respect to the possible materials and microstructures for producing corresponding surface wave conductors.

A local coil may have, as mentioned above, a fixing device for fixing the local coil on an examination object, in order to fix the local coils directly on the examination object, (e.g., the patient or the subject), or to fix the local coils indirectly on a patient bed on which the examination object is located. The metamaterial signal conductor may be arranged on such a fixing device, or the fixing device has a corresponding metamaterial signal conductor. In other words, the metamaterial signal conductor is mounted on the fixing device in some way, and may be integrated therein. The fixing device may, for example, itself be made at least partially of such a metamaterial or may be provided at least sectionally with a corresponding micro-fine structure, e.g., along a strip forming the metamaterial signal conductor.

The fixing devices may be a variety of elements that may be used to fix the local coil directly on the examination object or on a patient bed on which the examination object is positioned, such that the local coil may not be moved relative to the examination object without releasing the fixing device. The fixing device may include a fixing belt. Such fixing belts are also already commonplace and are fastened for example on a patient bed. At least one strip-shaped metamaterial signal conductor may extend along such a fixing belt. As will be illustrated below with reference to exemplary embodiments, this has particular advantages, since simultaneously with the fixing of the local coils, a corresponding coupling of the metamaterial signal conductors may also be provided and thus additional effort for cabling is dispensed with.

The fixing device may furthermore have an item of clothing that may be connected releasably to the antenna elements of the local coil and/or a blanket that may be connected releasably to the antenna elements. Corresponding, strip-shaped, metamaterial signal conductors may also be attached to or incorporated in the blanket or item of clothing, (e.g., a T-shirt, jogging bottoms or the like), in which the local coil may be integrated directly. Likewise possible is a combination of the various fixing devices, for example of items of clothing and/or blankets, and additional fixing belts.

The fixing device may have a coupling element for coupling the metamaterial signal conductor to the fixing device with a further metamaterial signal conductor. Such a further metamaterial signal conductor may be a metamaterial signal conductor of another fixing element, for example, to permit a transition from a metamaterial signal conductor in an item of clothing or on a blanket to a metamaterial signal conductor of a fixing belt and to couple them together for signaling purposes, such that a signal may be coupled unavoidably from one metamaterial signal conductor into the other metamaterial signal conductor or back.

The further metamaterial signal conductor may also be a metamaterial signal busbar. This is because the magnetic resonance system may be equipped with such a metamaterial signal busbar, which may be coupled for signaling purposes to a number of metamaterial signal conductors, for example of a plurality of different local coils. Such a metamaterial signal busbar may be arranged on a patient bed.

A coupling element on a fixing device may in particular be a coupling region on the fixing device that is suitable for coupling to a corresponding negative feedback element or negative feedback region, which interacts with the coupling element. An example of such a coupling region may be a touch-and-close region, with which the fixing device may in turn be connected to another element, for example a further fixing element, and/or to a corresponding region on the patient bed, such that at the same time, a coupling for signaling purposes to a further metamaterial signal conductor is provided.

In an embodiment, the metamaterial signal conductor is arranged on a first surface of the fixing device. The coupling element may be configured such that the first surface, in the case of a coupling to a further metamaterial signal conductor, rests against the further metamaterial signal conductor. That is to say, the direct contact between both metamaterial signal conductors leads to cross-coupling of a signal from the first metamaterial signal conductor to the second metamaterial signal conductor or vice versa.

In particular, if the magnetic resonance system has a metamaterial signal busbar, the system may also have a number of coupling units. The coupling units may also be arranged on a patient bed, e.g., displaceably along the metamaterial signal busbar. The coupling units may also serve for coupling a corresponding number of metamaterial signal conductors to the metamaterial signal busbar. By way of example, in each case, one coupling unit may be used to couple exactly one metamaterial signal conductor to the metamaterial signal busbar, where coupling for signaling purposes and at the same time mechanical coupling of the fixing device on which the metamaterial signal conductor is arranged take place. This is advantageous especially if the metamaterial signal conductors extend along the fixing belts that may be fixed and fastened directly on the patient bed using the coupling units, and at the same time, coupling for signaling purposes of the metamaterial signal conductors of the individual local coils to the metamaterial signal busbar on the patient bed takes place.

Independently of whether the coupling between a first metamaterial signal conductor and a further metamaterial signal conductor (e.g., a metamaterial signal busbar) takes place using coupling elements on the fixing device and/or using the previously described coupling units of the magnetic resonance system, (e.g., the patient bed), transition elements may be used. The transition elements are configured such that as a result, the wave propagation direction is changed or the wave propagation is deflected, for example by 90°. Such transition elements thus initially couple the signal that arrives longitudinally to a specific first direction along the strip-shaped metamaterial signal conductor out of the first metamaterial signal conductor, change direction, and couple the signal subsequently into the further metamaterial signal conductor or metamaterial signal busbar, which may extend longitudinally to a different direction than the first metamaterial signal conductor.

Such a transition element may, in particular, also be part of a coupling unit or be arranged to match a coupling element on the fixing device such that the transition element, in the case of a coupling between two metamaterial signal conductors, automatically comes to be positioned correctly. One example of such a transition element is a helically twisted metamaterial transition region or metamaterial signal conductor, as will be explained below with reference to figures.

It is possible using the metamaterial signal conductors used to establish a communication network in which a large number of local coils are connected to the local coil communication interface or to its components such as RF transmitting device, RF receiving device, control device, etc. For controlling the signaling traffic, in particular, if bidirectional transmission of signals is also desired, in order to receive not only raw data from the local coils but also to transmit at least control data to the local coils or to transmit even radio-frequency signals via the local coils, the magnetic resonance system may be equipped with a suitable signal control device (or network controller). The signal control device may be used in that case to control the signal exchange via the metamaterial signal conductor or conductors, in particular, via one metamaterial signal busbar and a plurality of metamaterial signal conductors of the individual local coils that are coupled thereto.

The signal control device may be constructed in a manner similar to a wireless transmission, since even in a wireless network, it is important to take care that collision-free transmission of the signals or data packets between the individual components of the network takes place. Therefore, suitable methods and control devices and control protocols may be used here, as are known from diverse wireless networks, such as WLAN, Bluetooth, etc., but also from wired networks, such as, for example, Ethernet, etc.

The signal control device, in particular, network controller, may be arranged in or on the local coil communication interface. Alternatively or additionally, a local coil itself may also have a corresponding signal control device that is configured to provide that, during signal transmission, anti-collision protocols and addressing protocols are observed. In particular, signal control devices, which are arranged in or on the local coil communication interface and in the local coil, may interact for collision-free transmission of the signals or data packets, or the signal control device is arranged in a distributed manner. The signal control device has, for example, interacting components in or on the local coil communication interface and in the local coil. If a plurality of local coils is used, a plurality of local coils may be equipped with corresponding signal control devices or components thereof.

Depending on the frequency range used, the desired signals, e.g., the control signals or radio-frequency signals or raw data, are transformed accordingly to the transmission frequency range. One possibility is analog signal modulation, in particular, for transmitting received magnetic resonance signals that may be converted from the MHz range into the desired GHz band range using analog signal modulation. In one alternative, first an analog-to-digital conversion of the signals to be transmitted takes place, followed for example by digital data compression and digital modulation within the transmission frequency range.

In order to carry out such a conversion, the local coil may have a signal preprocessing device, which includes at least one of the following components: (1) a preamplifier, which may serve for example for preamplifying the received magnetic resonance raw data; (2) an analog signal converter or, alternatively, an analog-to-digital converter and a corresponding modulator; or (3) a signal control unit, which may interact in particular with the signal control device of the magnetic resonance system already explained above, in order to coordinate the transmission of the signals via a network formed by the metamaterial signal conductors. By way of example, such a signal control unit may operate as a client that is driven by a master unit of the signal control device and may transmit signals or receive signals either upon request by the signal control unit or automatically, for example at regular intervals, at precisely defined timeslots.

Such a signal preprocessing unit may be arranged for signaling purposes upstream of the metamaterial signal conductor or also of the adapter device that serves for feeding the signals to the metamaterial signal conductor. However, depending on the construction, the adapter device may also be part of the signal preprocessing unit or be integrated therein. Furthermore, the signal preprocessing unit may have further components, such as various further sensors. Example sensors include, for example, temperature sensors, magnetic field sensors (field probes), motion sensors (e.g., acceleration sensor), respiratory sensors and heartbeat sensors or the like. All these signals of various sensors may be processed and transmitted together with the magnetic resonance signals.

A plurality of local coils may also be coupled together such that the plurality of local coils is assigned a common signal preprocessing unit. It is likewise possible for a plurality of local coils together to use at least parts of the signal preprocessing unit. For example, each local coil may have its own preamplifier but a common signal control unit. The components of the signal preprocessing unit mentioned here do not necessarily have to be incorporated in one module, but may also be distributed among a plurality of smaller modules that are arranged at different locations on the local coil, but are interconnected for signaling purposes.

The local coil may also have a suitable energy store, for example, a battery, in particular a rechargeable battery, a supercapacitor, or a different energy store, such as for example hydrogen cells or the like. The energy store may be interchangeable and/or recharging is possible, for example, when the local coil is not used, by coupling the store, for example using a connector or even using the metamaterial signal conductor, to a corresponding charging unit. Furthermore, it is also possible for the local coil to obtain energy using wireless energy transfer systems, for example, with known systems for resonant inductive coupling, or for obtaining energy from the radio-frequency output of a fixedly mounted radio-frequency transmission coil (for example the body coil) and/or by way of the activities of the magnetic field gradients. It is likewise possible to obtain energy thermally using infrared radiation or visible light. Furthermore, a combination of various energy generation systems and an energy store are realizable.

DETAILED DESCRIPTION

Figure 1:
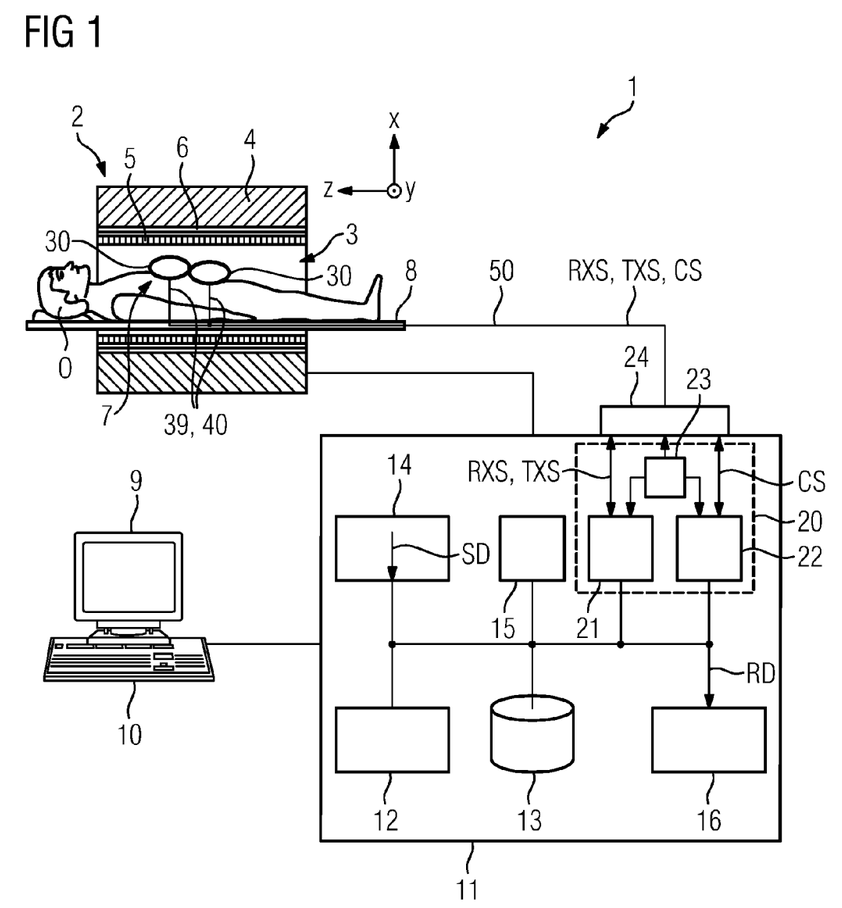
FIG. 1 depicts a schematic illustration of an exemplary embodiment of a magnetic resonance system.

FIG. 1 depicts a magnetic resonance system 1 (referred to in short as "MR system" below). The system includes the actual magnetic resonance scanner 2 with a measurement space 3 or the patient tunnel, which extends in the z direction and into which an examination object O (in this case a patient or subject) may be moved on a patient bed 8.

The magnetic resonance scanner 2 may be equipped with a main field magnetic system 4, a fixedly mounted RF antenna system 5 (e.g., a body coil 5 or whole body coil), a gradient system 6, and a local coil arrangement 7. The construction of the local coil arrangement 7 and its connection to further components of the magnetic resonance system 1 will be explained in more detail below.

In most cases, the fixedly mounted RF antenna system 5 is used to transmit RF signals (e.g., the $B_1$ field), and the local coils 30 of the local coil arrangement 7 are used for receiving the magnetic resonance measurement signals RXS. In principle, however, the fixedly mounted RF antenna system 5 may also be used as an RF receiving antenna system, and the local coils 30 as RF transmitting antennas, as long as the coils 30 are switchable in each case to different modes of operation. The magnetic resonance scanner 2 may also have a different construction, for example, having a patient space that is open on one side.

The MR system 1 furthermore has a central control device 11, which is used to control the MR system 1. The central control device 11 includes a sequence control unit 14 for pulse sequence control. The latter is used to control the sequence of radio-frequency pulses (RF pulses) and of gradient pulses in dependence on a selected magnetic resonance measurement sequence. The control parameters for the magnetic resonance measurement sequence may be predetermined for example in a measurement protocol or control protocol. A plurality of measurement protocols or control protocols is stored for example in a memory 13 for selection by a user and modifiable.

In order to control the gradient coils of the gradient system 6, the control device 11 has a gradient system interface 12. The components of the interface are used to generate the required gradient pulses, which are subsequently fed to the various gradient coils of the gradient system 6, or the desired gradient voltages are applied to the gradient coils.

The central control device 11 has a first radio-frequency transmitting/receiving device 15 for outputting RF pulses and receiving magnetic resonance signals, e.g., raw data, via the fixedly mounted RF antenna system 5. The transmitting part of the radio-frequency transmitting/receiving device 15 generates the RF pulses, amplifies them and feeds them, via a suitable interface, into the RF transmitting antenna system 5. The radio-frequency transmitting part may include a large number of components, among other small signal generators, which provide the appropriate radio-frequency pulses are generated initially with a low amplitude, and suitable radio-frequency amplifiers for feeding the radio-frequency pulses into the antennas with the required power. Also included are monitoring components, which are used to provide that the radio-frequency output falls within the limit values specified by the specific absorption rate (SAR) standards, etc.

The receiving part of the radio-frequency transmitting/receiving device 15 may, in coordination with the transmitting of the RF pulses and gradient pulses, receive the magnetic resonance signals. Accordingly, the receiving part includes a large number of receiving channels, in which the magnetic resonance signals, which are received by the individual antennas of the receiving antenna system and, if needed, further preprocessed, are received and further processed, in particular, amplified and digitized.

The sequence control unit 14 communicates in a suitable fashion, for example, by transmitting sequence control data SD, with the gradient system interface 12 and the radio-frequency transmitting/receiving device 15 for transmitting the pulse sequences.

In order to also be in a position to transmit radio-frequency pulses or receive primarily magnetic resonance measurement signals RXS or raw data via the local coil arrangement 7, the central control device 11 additionally has a second radio-frequency transmitting/receiving device 21 with a transmitting part and a receiving part. In principle, the transmitting part and the receiving part may have the same or similar construction as the corresponding parts of the first radio-frequency transmitting/receiving device 15 for the fixedly mounted RF antenna system 5. In this case, the components are provided in each case with a suitable interface for communicating with the local coils or are configured as part of the local coil communication interface 20.

It is also possible for the first and the second radio-frequency transmitting/receiving device 15, 21 to refer back to the same components that, depending on the current requirement, are connected in via corresponding communication paths or interfaces for operating the fixedly mounted radio-frequency antenna system 5 or the local coil arrangement 7. By way of example, a common transmitting part of a common radio-frequency transmitting/receiving device for transmitting the pulses may be coupled to the fixedly mounted RF antenna system 5, and the receiving part is connected in as part of the local coil communication interface 20 in a suitable fashion.

The local coil communication interface 20 additionally has a local coil control device 22, which may be used to transmit in a suitable fashion control signals CS to the local coils 30 of the local coil arrangement 7 in order to switch them to specific states, for example, from a transmitting state to a receiving state, or in order to detune them for complete deactivation or tune them to an exact magnetic resonance frequency, etc. The local coil control device 22 may also receive or request status signals from the local coils 30 so as to be informed about the current state of the local coils 30.

A further component of the local coil communication interface 20 is a signal control device 23, which forms a network controller, controls the communication via communication channels using the metamaterial signal conductors 39, 50, and provides that signal collisions do not take place. The signal control device 23 may be coupled for example, as depicted in FIG. 1, to the local coil control device 22 and the second radio-frequency transmitting/receiving device 21 in order to control their activities relating to the receiving and transmitting of the signals RXS, TXS, CS.

One component is an adapter device 24, which is connected to the local coil communication interface 20 and feeds all signals RXS, CS, which are intended to be transmitted by the local coil communication interface 20 to the local coil arrangement 7, into a metamaterial signal conductor 50 in a suitable fashion. The illustrated example is a metamaterial signal busbar 50, which is guided to the patient bed 8, is guided along it, and is coupled at various locations to metamaterial signal conductors 40 that lead to the individual local coils 30 of the local coil arrangement 7.

An image data generation unit 16 receives the raw data RD acquired for example via the first and/or second radio-frequency transmitting/receiving device 15, 21 and reconstructs therefrom the desired magnetic resonance image data of the object O. The image data may be output via an image data interface and may be stored, for example, in a memory 19 and/or be output on a screen 9. It is likewise possible for the image data to be stored in external memories via a network and/or to be output on corresponding output devices or be presented on a monitor for the purpose of making a diagnosis.

The central control device 11 may be operated via a terminal with an input unit 10 and a display unit 9, which terminal is also used so that the entire MR system 1 may be operated by an operator. It is also possible for the image data to be displayed on the display unit 9, and measurements may be planned and started using the input unit 10, or if needed in combination with the display unit 9.

The MR system 1, the magnetic resonance scanner 2, and the control device 11 may have a large number of further components, such as, for example, a network interface, in order to be able to connect the entire system to a network and exchange raw data and/or image data or parameter maps, but also further data, such as for example patient-relevant data or control protocols. The basic process of such a magnetic resonance measurement and the components for controlling it are, however, known to the person skilled in the art.

In particular, the architecture of the local coil communication interface 20, illustrated with reference to FIG. 1, is one exemplary embodiment, and there are several possibilities for mounting the local coils 30 on the required components. An adapter device 24 having one or more adapters is present to transmit the signals via a metamaterial signal conductor 50 to the local coils 30.

Figure 2:
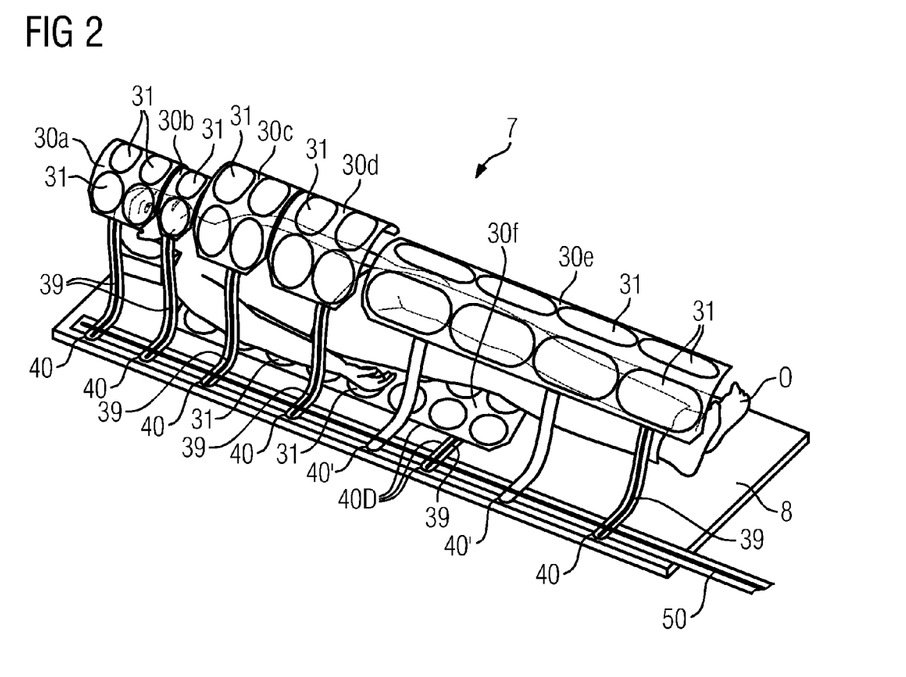
FIG. 2 depicts a schematic illustration of an exemplary embodiment of a local coil arrangement.

One possible construction of a local coil arrangement 7 is illustrated in more detail in FIG. 2. In this case, a patient O is lying on a patient bed 8. Located underneath the patient O, on the patient bed 8, is a spine local coil 30_f_, which extends over the entire back, in order to produce, for example, detailed recordings of the complete spinal column. The individual antenna elements 31 of the spine local coil 30_f_ are integrated in a blanket 40D, which in the present case serves as a fixing device 40D, since the blanket 40D is fixed on the surface of the table 8 and thus also relative to the patient O located thereon using touch-and-close strips or the like. Furthermore, a local coil 30_a_ is located above the facial area of the patient O, a further local coil 30_b_ in the neck region, a local coil 30_c_ in the chest area, a local coil 30_d_ in the stomach area, and a further local coil 30_e_, which is designed in the manner of a relatively long blanket, covers the legs of patient O. Patient O is thus covered completely by local coils 30_a_, 30_b_, 30_c_, 30_d_, 30_e_ even from the top. Each of the local coils 30_a_, 30_b_, 30_c_, 30_d_, 30_e_, 30_f_ has, in a conventional manner, a plurality of antenna elements 31. The antenna elements 31 are in each case connected to a signal preprocessing unit. A plurality of antenna elements 31 of a local coil 30_a_, 30_b_, 30_c_, 30_d_, 30_e_, 30_f_ may be coupled to a common signal preprocessing unit.

The local coils 30_a_, 30_b_, 30_c_, 30_d_, 30_e_, which are located on top of the patient O, are in each case fixed on patient O using fixing belts 40, 40', and are guided away laterally from the patient O on both sides (FIG. 2 schematically depicts the fixing belts 40, 40' on the front side). The fixing belts 40, 40' are connected or fixed to the patient bed 8 in a suitable fashion and, for example, fastened such that the relevant local coils 30_a_, 30_b_, 30_c_, 30_d_, 30_e_ are sufficiently fixed in place on patient O and may not move during the examination. Corresponding fixing capabilities will be explained below with reference to FIGS. 4 and 5.

As will also be explained below in more detail, metamaterial signal conductors 39, which are incorporated in the material of the fixing belts 40 or are fixedly connected thereto, extend at least along part of the fixing belts 40. The metamaterial signal conductors 39 are thin or flat and just as flexible as the fixing belts 40, so that they do not obstruct the handling of the fixing belts 40.

For most local coils 30_a_, 30_b_, 30_c_, 30_d_, in each case two fixing belts on both sides of the patient suffice, while other longer local coils, such as the leg coil 30_e_, are provided over their lengths at several locations with fixing belts 40, 40'. As is illustrated with reference to the leg local coil 30_e_, it suffices if one metamaterial signal conductor 39 extends along one of the fixing belts 40. However, it is possible for a plurality of metamaterial signal conductors to lead to one local coil. All metamaterial signal conductors 39 may be guided on the same side along the fixing belts 40, and may then, during fixing on the patient bed, be coupled to a metamaterial signal busbar 50, which is guided along the patient bed 8 and may be mounted on the patient bed 8 at the same time. In that case, the signals transmitted via the metamaterial signal conductors 39 may be coupled into the metamaterial signal busbar 50, or signals may be coupled out of it and transferred to the local coil 30a, 30b, 30c, 30d, 30e, 30f via the metamaterial signal conductors 39.

The spine local coil 30f located under the patient also has such a metamaterial signal conductor 39, which is guided away from the local coil 30f on a lug formed on the blanket 40D and is likewise coupled to the metamaterial signal busbar 50.

Figure 3:
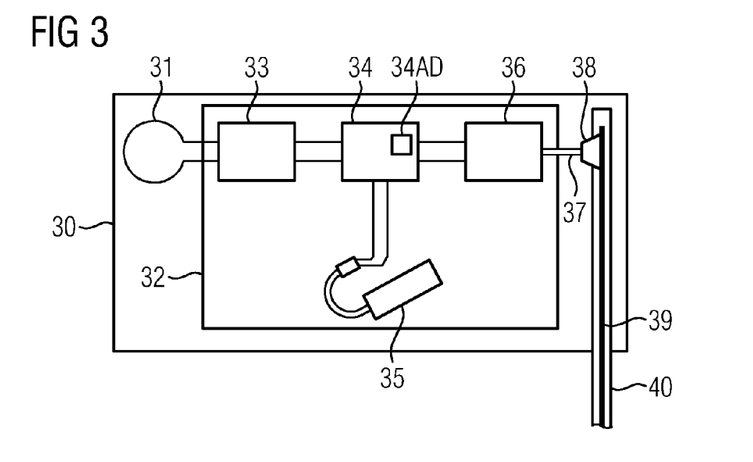
FIG. 3 depicts a schematic illustration of an exemplary embodiment of a local coil.

FIG. 3 illustrates an exemplary embodiment for a signal preprocessing unit 32 of a local coil 30. For the sake of simplicity, only one antenna element 31 is depicted. However, as already explained in connection with FIG. 2, it is certainly also possible for a plurality of antenna elements 31 to be coupled to the same signal preprocessing unit 32.

The signal preprocessing unit 32 has a preamplifier/tuning and detuning unit 33. This preamplifier/tuning and detuning unit 33 serves for pre-amplifying received magnetic resonance measurement signals RXS and for detuning or precisely tuning the coil 31, depending on the received control commands. In the case of a local coil, which is also intended to be suitable for transmitting radio-frequency signals TXS ($B_1$ pulses), the local coil may also have a suitable switch unit that may likewise be integrated in the unit 33.

The signal preprocessing unit 32 additionally has a signal converting and signal control unit 34. The signal converting and signal control unit 34 may have an analog-to-digital converter 34AD for firstly digitizing the magnetic resonance measurement signals RXS received from the preamplifier 33.

A further component of the signal preprocessing unit in the present case is a microwave modulator 36, which modulates the signals to be transmitted to the desired carrier frequency, (e.g., in a range above 10 GHz, above 15 GHz, above 20 GHz, or in the 60 GHz range), where the microwave modulator modulates the signals onto the carrier frequency.

The signal converting and signal control unit 34 is additionally coupled in the present case to an energy storage unit 35, (e.g., a battery), and also supplies the required energy to the further components such as the preamplifier/tuning and detuning unit 33 or the microwave modulator 36. When the local coil is not in use, the battery is rechargeable via a suitable connection, or the battery may be a removable storage battery that may be exchanged between two measurements for a freshly charged storage battery.

At the end of the signal chain, downstream of the microwave modulator 36, a digital signal is present that is modulated onto a carrier frequency in the desired transmission band. Where signals, for example control signals, are also intended to be received, the microwave modulator may also have a desired demodulator component to pass the control signals demodulated from the carrier to the signal converting and signal control unit 34, which controls, for example, the preamplifier/tuning and detuning unit 33. Where the local coil 30 is intended to serve as a RF transmission coil, the required RF pulses may likewise be transferred via the components in a similar manner.

In principle, it is also possible for a further signal processing unit to be provided in the local coil, which signal processing unit then provides the transmission of radio-frequency signals to the antenna elements 31, where it may also use components of the signal preprocessing unit 32, in particular the required components for tuning and detuning the local coil and the control electronics and the energy source etc.

Alternatively to the digital conversion of the magnetic resonance measurement signals RXS to a carrier frequency in that GHz range, as illustrated here, analog signal conversion is also possible. In that case, the signal preprocessing unit 32 may have, downstream of the preamplifier, a corresponding analog signal converter.

The signals converted to the GHz range are in the present case transferred, via a short coaxial line 37 or the like, to an adapter 38, which feeds the signals into the metamaterial signal conductor 39, which extends, for example, along a fixing belt 40. Such a metamaterial signal conductor 39 may be constructed such as is described, for example, in the article by J. Hendry already mentioned above. Likewise possible materials are here, as are explained in the article "A Novel Technique Enabling the Realisation of 60 GHz Body Area Networks" by J. E. Turner, M. S. Jessup and K.-F. Tong, published in: Preceding BSN '12 Proceedings of the 2012 Ninth International Conference on Wearable and Implantable Body Sensor Networks, pages 58-62, IEEE Computer Society Washington, D.C., USA©2012. This article describes that the materials used therein make possible a transmission, with only small losses, in the range above 23 GHz or also in the range of 60 GHz, where the materials in particular also achieve strong attenuation in the desired range of below 10 GHz.

The metamaterial signal busbar 50 may have the same construction, e.g., be structured in the same manner, as the metamaterial signal conductor 39. However, different realizations are also possible in principle. All metamaterial signal conductors 39, 50 operate in the same frequency range or have as low an attenuation as possible in the frequency band used.

Adapters that may be used are, in principle, conventional coaxial-to-waveguide adapters, for example a Waveguide to SMA Model V4607, Narda Microwave—East, 435 Moreland Road Hauppauge, N.Y. 11788 USA. It is provided here that the lowest point of its aperture is aligned with the surface of the material of the metamaterial signal conductor. In this manner, the signals in the GHz range from a coaxial conductor may be efficiently coupled into the metamaterial signal conductor.

In the same way, it is also possible to couple out the signals, such that consequently the adapter device 24 at the local coil communication interface 20 of the central control device 11 of the magnetic resonance system 1 may be equipped with corresponding adapters or, in the case where only one metamaterial signal busbar 50 is used, with one corresponding adapter.

Figure 4:
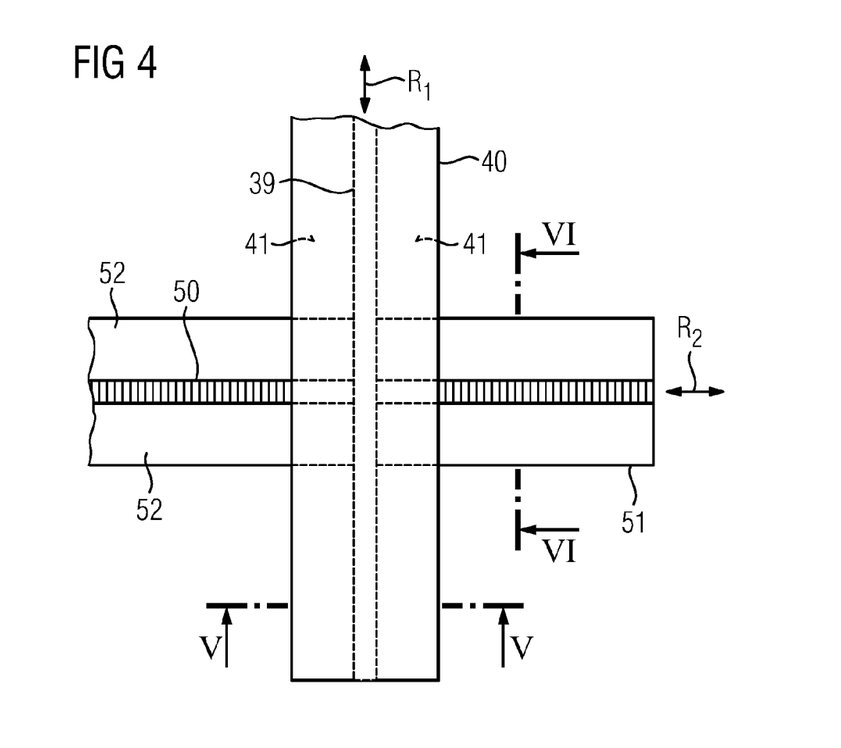
FIG. 4 depicts a schematic illustration of a first exemplary embodiment of a coupling between a metamaterial signal conductor of a fixing belt of a local coil on a patient bed and a metamaterial signal busbar.
Figure 5:
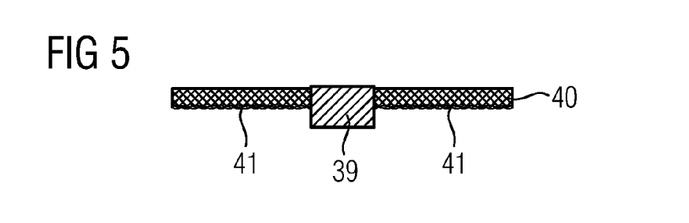
FIG. 5 depicts a cross section embodiment of the fixing belt according to FIG. 4.
Figure 6:
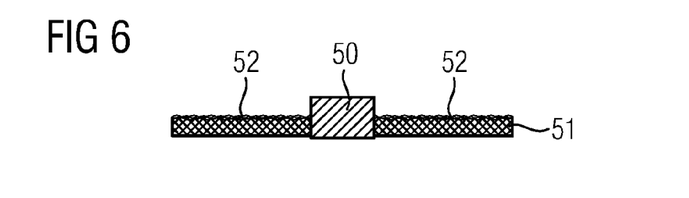
FIG. 6 depicts a cross section embodiment of the metamaterial signal busbar according to FIG. 4.

FIGS. 4 to 6 illustrate an exemplary embodiment of how mechanical coupling of a fixing belt 40 to the patient bed and, at the same time, coupling of the metamaterial signal conductor 39 of the fixing belt 40 to the metamaterial signal busbar 50 of a fixing strip 51 to the patient bed 8 is possible. FIG. 4 illustrates a top view of a point of intersection of the fixing belt 40 and the metamaterial signal busbar 50. FIG. 5 depicts a cross section of the fixing belt 40 along the section line V-V in FIG. 4, and FIG. 6 depicts a cross section of the fixing strip 51 attached to the patient bed 8 along the section line VI-VI in FIG. 4 with the metamaterial signal busbar 50 and two adjoining fixing regions 52.

As may be seen from these figures, the fixing belt 40 has a central strip that was produced such that it forms the metamaterial signal conductor 39. To the right and to the left of the metamaterial signal conductor 39, there are fixing regions 41 that are configured as touch-and-close regions 41, for example having loops. While fixed to the patient bed 8, two fixing regions 52 correspondingly extend next the metamaterial signal busbar 50, which fixing regions 52 are likewise configured as (counter) touch-and-close regions 52 and are constructed such (for example, having suitable small hooks) that they connect to the touch-and-close regions 41 of the fixing belt 40.

As may be seen in FIG. 4, the fixing belt 40 may be fixed simply on the patient table by overlaying the touch-and-close regions 41, 52 in the manner of a cross to form a hook-loop connection. At the same time it is provided that the metamaterial signal conductor 39 comes to rest with its surface on the intersection point directly on the surface of the metamaterial signal busbar 50. A signal, which for example originates at the local coil, propagates along the direction $R_1$ along the metamaterial signal conductor 39 and does not laterally go beyond it. As soon as the signal reaches the intersection point with the metamaterial signal busbar 50, the signal also cross-couples, among others, into the metamaterial signal busbar 50 and spreads, in a point-type manner, in both longitudinal directions $R_2$ of the metamaterial signal busbar 50, and thus also in the direction toward the adapter device 24 of the local coil communication interface 20 of the central control unit 11 (see FIG. 1), such that the signal may be coupled out there again.

This applies to all signals that arrive, via the fixing belts 40 with the associated metamaterial signal conductors 39, from the various local coils 30*a*, 30*b*, 30*c*, 30*d*, 30*e*, 30*f*. As already mentioned above, it is merely necessary to provide, by a suitable network controller 23, that anticollision protocols and addressing protocols are observed, which may be realized easily with conventional methods from radio networks, however.

Figure 7:
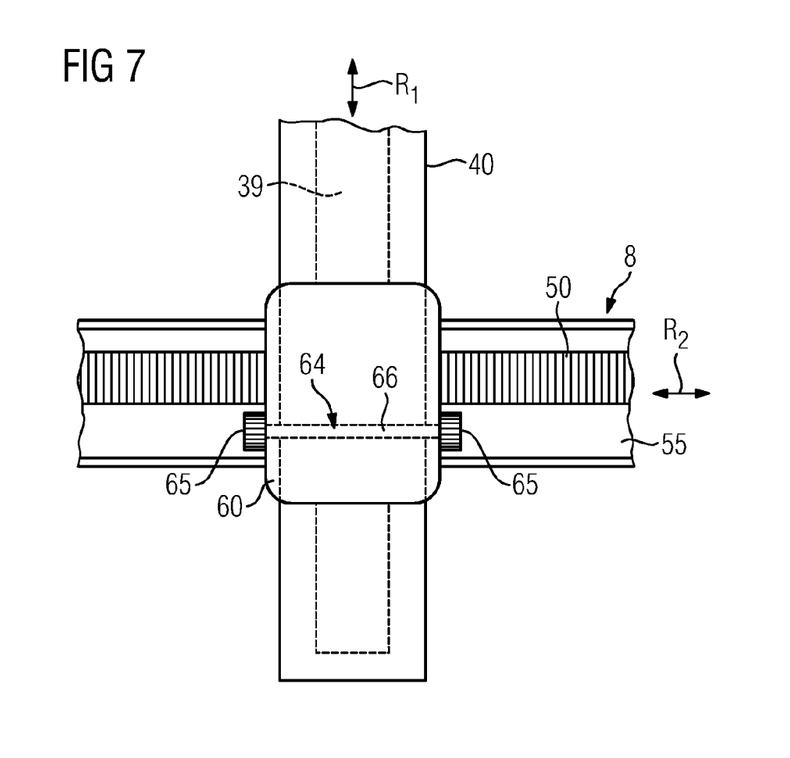
FIG. 7 depicts a schematic illustration of a second exemplary embodiment of a coupling between a metamaterial signal conductor of a fixing belt of a local coil on a patient bed and a metamaterial signal busbar using a coupling unit.
Figure 8:
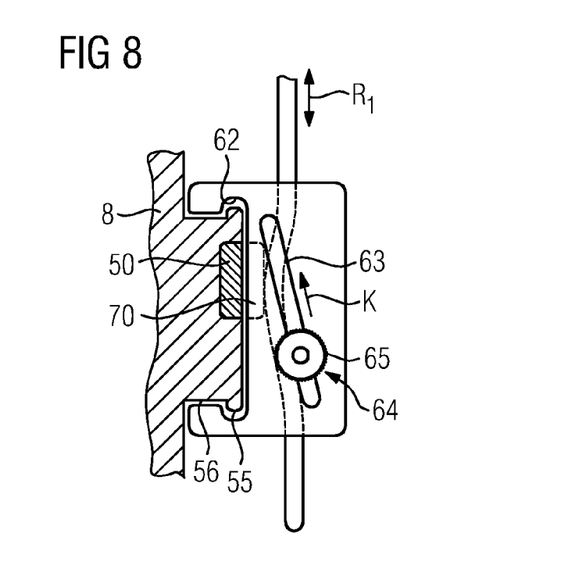
FIG. 8 depicts a lateral top view embodiment of the coupling unit with a cross section of the metamaterial signal busbar according to FIG. 7.

FIGS. 7 and 8 illustrate a further variant for fixing the fixing belts to the patient bed, with which more secure fastening of the fixing belts 40 is possible (as compared to the variant according to FIG. 4). A type of slide rail 55 is arranged on a longitudinal side of the patient bed 8, which slide rail has a T profile with two profiled grooves 56 facing up and down. Arranged on the slide rail 55 of the patient bed 8 are a plurality of coupling units 60 that have, toward the slide rail 55, in each case one mating profile 62, which may engage in the T profile 55 such that the coupling units 60 may be displaced along the slide rail 55 in the direction $R_2$. The coupling units 60 may thus be moved to where they are needed for securing a fixing belt 40.

Instead of the illustrated T profile, a different profile with similar action, for example, a dovetail profile, may be used. A metamaterial signal busbar 50 is incorporated along the slide rail 55 on the outside.

FIG. 7 illustrates a top view of such a coupling unit 60, and FIG. 8 illustrates a cross section of the slide rail 55, arranged at the patient bed 8, and the metamaterial signal busbar 50 in a lateral top view of a coupling unit 60.

The fixing belt 40 is here constructed in principle again like the fixing belt 40 according to FIG. 4, although the touch-and-close regions may be omitted. For example, it suffices if the fixing belt 40 has, on its underside facing the patient, a metamaterial signal conductor 39. The fixing belt 40 is inserted from above into a slot in a housing of the coupling unit 60 for fixing purposes and dangles out of the coupling unit 60 at the bottom. For clamping the fixing belt 40, the coupling unit 60 is equipped with a clamping element 64, which has a clamping bar 66 that extends over the entire width of the coupling unit 60 transversely through a housing of the coupling unit 60 and transversely with respect to the fixing belt 40. The clamping bar 66 has, on both ends, outside of the housing of the coupling unit 60 in each case knurling wheels 65, by which the bar 66 may be gripped and displaced diagonally upward along a slotted link 63 situated in the housing of the coupling unit 60. In this manner, the fixing belt 40, which extends through the slot in the housing of the coupling unit 60 and is pulled sufficiently tight at the bottom, may be clamped tight. The fixing belt 40 is displaced in the process automatically toward the metamaterial signal busbar 50 in the slide rail 55.

In the exemplary embodiment illustrated, a signal transition element 70 is arranged additionally in the housing of the coupling unit 60 exactly at that spot at which the fixing belt 40 is clamped tight if the clamping element 64 is pulled up. This provides that the signal, which travels from the metamaterial signal conductor 39 in the longitudinal direction $R_1$ and is intended to be coupled into the metamaterial signal busbar 50, or vice versa, cross-couples better between the metamaterial signal conductors. The signal transition element 70 may likewise be a metamaterial signal conductor section. The signal transition element 70 may be arranged on the coupling unit 60 such that it rests directly against the metamaterial signal busbar 50, e.g., slides on it (in FIG. 8, for the sake of clarity, a small distance is depicted). However, alternatively a further clamping device may also provide that the signal transition element 70 is pressed down only when the coupling unit 60 is located at the appropriate position along the slide rail 55 in order to avoid friction between the metamaterial signal busbar 50 and the transition elements 70 of the coupling units 60.

Figure 9:
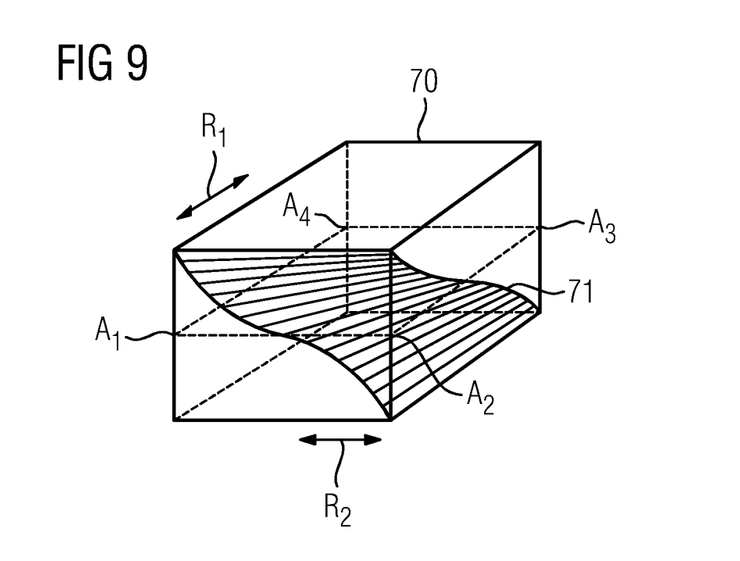
FIG. 9 depicts a schematic perspective illustration of an exemplary embodiment of a signal transition element for a coupling unit according to FIG. 7.
Figure 10:
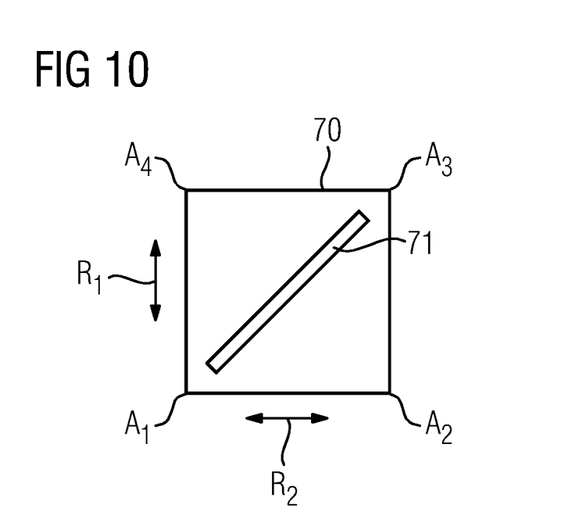
FIG. 10 depicts a section through a signal transition element according to FIG. 9.

FIGS. 9 and 10 illustrate an embodiment of such a signal transition element 70. FIG. 9 depicts a schematic perspective illustration of the signal transition element 70, and FIG. 10 depicts a section through the planes of the points $A_1$, $A_2$, $A_3$, $A_4$ in FIG. 9. As is depicted, the signal transition element 70 includes a small block in which a plane of a metamaterial signal conductor 71 is twisted helically such that the signal propagation direction is correspondingly parallel to the running direction $R_1$ (or extension direction) of the metamaterial signal conductor 39, on that side on which the transition element 70 rests against the metamaterial signal conductor 39 of the fixing belt 40, and runs in the running direction $R_2$ (or extension direction) of the metamaterial signal busbar 50 on the other side, on which the transition element 70 rests against the metamaterial signal busbar 50 of the patient bed 8. The metamaterial signal conductor 71 is helically twisted in the present case about 90°, within the signal transition element 70.

This is realizable, for example, by micro-patterning a block made of a suitable material, (such as using a laser or another suitable device), along the desired running direction of the metamaterial signal conductor 71. Alternatively, the metamaterial signal conductor 71 in the signal transition element 70 may be constructed of a thin, micro-patterned film, which is correspondingly twisted helically and is held in two corresponding contoured material halves. That provides the metamaterial signal conductor 71 and the material halves may be adhesively bonded together to form a block, for example.

Alternatively, the transition element 70 may be constructed from a plurality of thin films, which are, for example, adhesively bonded one above another, where in each plane the running direction or the micro-patterning is twisted with respect to the plane located above it, until, for example, the uppermost and the bottommost film have a rotation of 90° with respect to one another. In that case, the signal travels to and from in a meandering shape on the individual planes, defined by the films, where the running direction correspondingly slowly rotates.

In summary, the detailed methods and structures described above are exemplary embodiments, and that the basic principle may also be varied widely by the person skilled in the art. In particular, the embodiments may also be employed in magnetic resonance imaging in the non-medical field. It is furthermore also possible, for example, for a transition element to be used in the exemplary embodiments according to FIGS. 7 and 8, which does not cause the running direction to rotate. Likewise, however, in the exemplary embodiment according to FIGS. 4 to 6, a transition element having a rotation in the running direction may also be used if the transition element may be fixed on the patient bed, for example also using corresponding touch-and-close elements between the fixing belt 40 and the touch-and-close strips 52, such that it comes to rest exactly between the metamaterial signal conductors 39 of the fixing belt 40 and the metamaterial signal busbar 50 located on the patient bed and is constructed to be relatively thin. For the sake of completeness, the use of the indefinite article "a" or "an" does not exclude that the relevant features may also be present as multiples. The term "unit" likewise does not exclude a plurality of components which may, if appropriate, also be spatially distributed.

It is to be understood that the elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

While the present invention has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A local coil comprising:
   magnetic resonance antenna elements;
   a metamaterial signal conductor connected to the magnetic resonance antenna elements, the metamaterial signal conductor having a bandpass characteristic with a stopband below 10 GHz;
   a metamaterial signal busbar coupled to the metamaterial signal conductor; and
   an adapter device connected to the metamaterial signal busbar, the adapter device configured to couple signals into the metamaterial signal conductor, couple signals out of the metamaterial signal conductor, or couple signals into and out of the metamaterial signal conductor.

2. The local coil as claimed in claim 1, wherein the metamaterial signal conductor is strip-shaped.

3. The local coil as claimed in claim 1, wherein the metamaterial signal conductor forms a surface wave conductor.

4. The local coil as claimed in claim 1, further comprising a fixing device for fixing the local coil on an examination object, wherein the fixing device has the metamaterial signal conductor.

5. The local coil as claimed in claim 4, wherein the fixing device comprises a fixing belt along which the metamaterial signal conductor extends.

6. The local coil as claimed in claim 4, wherein the fixing device comprises an item of clothing connected to the local coil or a blanket connected to the local coil.

7. The local coil as claimed in claim 4, wherein the fixing device comprises a coupling element for coupling the metamaterial signal conductor to the metamaterial signal busbar.

8. The local coil as claimed in claim 7, wherein the metamaterial signal conductor is arranged on a first surface of the fixing device, and the coupling element is configured such that the first surface rests against the metamaterial signal busbar.

9. The local coil as claimed in claim 1, further comprising a signal preprocessing unit assigned to the local coil, the signal processing unit comprising at least one of the following components:
   a preamplifier;
   an analog signal converter;
   an analog-to-digital converter;
   a modulator;
   a signal control unit; or
   further sensors.

10. A magnetic resonance system comprising:
    a local coil communication interface; and
    a local coil having:
       magnetic resonance antenna elements;
       a metamaterial signal conductor connected to the magnetic resonance antenna elements, the metamaterial signal conductor having a bandpass characteristic with a stopband below 10 GHz;
       a metamaterial signal busbar coupled to the metamaterial signal conductor; and
       an adapter device connected to the metamaterial signal busbar, the adapter device configured to: (a) couple first signals out of a metamaterial signal conductor and transfer the first signals to the local coil communication interface, (b) couple second signals from the local coil communication interface into the metamaterial signal conductor, or (c) couple the first signals out of the metamaterial signal conductor and transfer the first signals to the local coil communication interface and couple second signals from the local coil communication interface into the metamaterial signal conductor.

11. The magnetic resonance system as claimed in claim 10, further comprising coupling units for coupling the metamaterial signal conductors to the metamaterial signal busbar.

12. The magnetic resonance system as claimed in claim 11, further comprising a signal control device for controlling a signal exchange via the metamaterial signal busbar.

13. The magnetic resonance system as claimed in claim 10, further comprising a signal control device for controlling a signal exchange via the metamaterial signal busbar.

14. A method for transmitting signals, the method comprising:
    providing a local coil having: (1) magnetic resonance antenna elements, (2) a metamaterial signal conductor connected to the magnetic resonance antenna elements, wherein the metamaterial signal conductor has a bandpass characteristic with a stopband below 10 GHz, (3) a metamaterial signal busbar coupled to the metamaterial signal conductor, and (4) an adapter device connected to the metamaterial signal busbar;
    coupling signals, by the adapter device of the local coil, into the metamaterial signal conductor, coupling signals out of the metamaterial signal conductor, or coupling signals into and out of the metamaterial signal conductor; and transmitting the signals between the local coil and a local coil communication interface of a magnetic resonance system via the metamaterial signal conductor.

15. The method as claimed in claim 14, wherein the metamaterial signal conductor is strip-shaped.

\* \* \* \* \*